(12) United States Patent
Yen

(10) Patent No.: US 11,260,110 B2
(45) Date of Patent: *Mar. 1, 2022

(54) NANOPARTICLES FOR THE THERAPEUTIC TREATMENT OF RADIATION-INDUCED SKIN ULCERS

(71) Applicant: Richard C. K. Yen, Yorba Linda, CA (US)

(72) Inventor: Richard C. K. Yen, Yorba Linda, CA (US)

(73) Assignee: PTLNV, LLC, series four (4), Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/505,257

(22) Filed: Jul. 8, 2019

(65) Prior Publication Data
US 2019/0328844 A1    Oct. 31, 2019

Related U.S. Application Data

(60) Continuation-in-part of application No. 15/233,779, filed on Aug. 10, 2016, which is a continuation-in-part of application No. 13/560,727, filed on Jul. 27, 2012, now abandoned, and a continuation-in-part of application No. 14/226,544, filed on Mar. 26, 2014, now Pat. No. 9,629,931, which is a continuation-in-part of application No. 12/927,543, filed on Nov. 16, 2010, now Pat. No. 9,226,898, and a continuation-in-part of application No. 13/560,727, filed on Jul. 27, 2012, now abandoned, and a continuation-in-part of application No. 13/604,770, filed on Sep. 6, 2012, now Pat. No. 9,351,925, and a continuation-in-part of application No. 13/605,765, filed on Sep. 6, 2012, now Pat. No. 9,504,641, said application No. 15/233,779 is a continuation-in-part of application No. 14/925,506, filed on Oct. 28, 2015, now abandoned, which is a continuation-in-part of application No. 13/560,727, filed on Jul. 27, 2012, now abandoned, and a continuation-in-part of application No. 13/604,770, filed on Sep. 6, 2012, now Pat. No. 9,351,925, said application No. 14/925,506 is a continuation-in-part of application No. 13/605,765, filed on Sep. 6, 2012, now Pat. No. 9,504,641, application No. 16/505,257, which is a continuation-in-part of application No. 15/618,234, filed on Jun. 9, 2017, now Pat. No. 10,603,287, and a continuation-in-part of application No. 14/953,066, filed on Nov. 27, 2015, now abandoned, which is a division of application No. 12/927,543, filed on Nov. 16, 2010, now Pat. No. 9,226,898, application No. 16/505,257, which is a continuation-in-part of application No. 15/238,928, filed on Aug. 17, 2016, now abandoned, which is a continuation of application No. 13/560,727, filed on Jul. 27, 2012, now abandoned, and a continuation-in-part of application No. 13/605,765, filed on Sep. 6, 2012, now Pat. No. 9,504,641, and a continuation-in-part of application No. 14/226,544, filed on Mar. 26, 2014, now Pat. No. 9,629,931, and a continuation-in-part of application No. 14/953,066, filed on Nov. 27, 2015, now abandoned, and a
(Continued)

(51) Int. Cl.
| | |
|---|---|
| A61K 38/38 | (2006.01) |
| A61K 38/36 | (2006.01) |
| A61K 9/00 | (2006.01) |
| A61K 9/10 | (2006.01) |
| A61K 9/16 | (2006.01) |
| A61K 9/51 | (2006.01) |

(52) U.S. Cl.
CPC .......... *A61K 38/385* (2013.01); *A61K 9/0019* (2013.01); *A61K 9/16* (2013.01); *A61K 9/5169* (2013.01); *A61K 38/38* (2013.01)

(58) Field of Classification Search
None
See application file for complete search history.

(56) References Cited

U.S. PATENT DOCUMENTS

| | | |
|---|---|---|
| 4,440,679 A | 4/1984 | Fernandes et al. |
| 5,679,377 A | 10/1997 | Bernstein et al. |

(Continued)

FOREIGN PATENT DOCUMENTS

| | | |
|---|---|---|
| WO | 2013036902 A1 | 3/2013 |

OTHER PUBLICATIONS

Wang, J., et al. 2006 Hernia 10: 502-506. (Year: 2006).*
(Continued)

*Primary Examiner* — Marsha Tsay
(74) *Attorney, Agent, or Firm* — David Guerra

(57) ABSTRACT

A method of treating radiation-induced skin toxicity or skin ulcers with nanoparticles after exposure to ionizing radiation and after an onset of radiation-induced skin toxicity or a radiation-induced skin ulcer by administering intravenously a suspension including fibrinogen-coated albumin nanospheres to a patient. A concentration of the suspension being sufficient to at least one of promote healing of the skin toxicity or reduce a size of the skin ulcer. The suspension can include fibrinogen-coated albumin nanospheres, sorbitol and/or caprylate. The suspension can be utilized for treating a patient to reduce an amount of blood loss in an organ of the patient or for treating a patient to mobilize stem cells or progenitor cells to accelerate healing of a wound.

17 Claims, 3 Drawing Sheets

Related U.S. Application Data continuation-in-part of application No. 14/925,506, filed on Oct. 28, 2015, now abandoned.

(60) Provisional application No. 62/733,468, filed on Sep. 19, 2018, provisional application No. 61/853,041, filed on Mar. 27, 2013, provisional application No. 61/573,630, filed on Sep. 10, 2011, provisional application No. 61/627,623, filed on Oct. 14, 2011, provisional application No. 62/364,764, filed on Jul. 20, 2016, provisional application No. 61/281,466, filed on Nov. 18, 2009.

(56) References Cited

U.S. PATENT DOCUMENTS

| | | | |
|---|---|---|---|
| 6,221,668 | B1 | 4/2001 | Ryan et al. |
| 6,262,019 | B1 | 7/2001 | Keller et al. |
| 6,264,988 | B1 | 7/2001 | Yen |
| 6,916,795 | B1 | 7/2005 | Youssef |
| 7,625,878 | B2 | 12/2009 | Stella et al. |
| 9,114,127 | B2 | 8/2015 | Yen |
| 9,226,898 | B1 | 1/2016 | Yen |
| 9,351,925 | B2 | 5/2016 | Yen |
| 9,629,931 | B2 | 4/2017 | Yen |
| 2002/0004522 | A1 | 1/2002 | Mueller et al. |
| 2002/0142046 | A1 | 10/2002 | Yen |
| 2003/0181378 | A1 | 9/2003 | Makishima et al. |
| 2004/0043077 | A1 | 3/2004 | Brown |
| 2004/0071715 | A1 | 4/2004 | Schwendeman et al. |
| 2009/0304804 | A1 | 12/2009 | Yen |
| 2009/0306186 | A1 | 12/2009 | Jackson et al. |
| 2011/0189299 | A1 | 8/2011 | Okubo et al. |
| 2011/0225661 | A1 | 9/2011 | Deng et al. |
| 2014/0030347 | A1 | 1/2014 | Yen |
| 2016/0045573 | A1 | 2/2016 | Yen |
| 2016/0082086 | A1 | 3/2016 | Yen |
| 2016/0354481 | A1 | 12/2016 | Yen |

OTHER PUBLICATIONS

European Commission, "Commission Implementing Decision (Feb. 12, 2015)", EU orphan designation No. EU/3/15/1442, Feb. 12, 2015.
European Medicines Agency, "Public summary of opinion on orphan designation", EMA/COMP/55779/2015, Committee for Orphan Medicinal Products, Mar. 30, 2015.
World Health Organization, "Guidelines on viral inactivation and removal procedures intended to assure the viral safety of human blood plasma products", Annex 4, WHO Technical Report, Series No. 924, 2004.
Hosseini et al., "Study of the Heat-Treated Human Albumin Stabilization by Caprylate and Acetyltryptophanate", Dept. of R&D, Blood Research and Fractionation Co., Tehran, Iran, Iranian Biomedical Journal 6 (4): /35-140 (Oct. 2002).
Dr. Anrei Gudkov, Radiation Sickness Cures and Anti-Radiation Pills, http://nextbigfuture.com/2009/07/radiation-sickness-cures-and-anti.html, Jul. 20, 2009.
Smiley et al., "Fibrinogen stimulates macrophate chemokine secretion through toll-like receptor 4" J Immunol. Sep. 1, 2001; 167(5) abstract.
Perdomo et al., "Quinine-induced thrombocytopenia: drug-dependent GPIb/IX antibodies inhibit megakaryocyte and proplatelet production in vitro". Blood Jun. 2, 2011 vol. 117 No. 225975-5986.
Reiter et al., "Vitamin E and excessive bleeding" Ugeskr Laeger, Dec. 5, 2005; 167(49) (abstract).
Manjunatha, Antiboagulant proteins from snake venoms:structure, function and mechanism Biochem J (2006) 397, 377-387.
Blajchman, 1996, "Evaluation of the in vivo Hemostatic Function of Human Platelets and Platelet Substitutes in a Thrombocytopenic Rabbit Model", In "Frozen Platelets and Platelet Substitutes in Transfusion Medicine" Mar. 7, 1996.

CDC, 2013, "Acute Radiation Syndrome Fact Sheet for Physicians", http://www.bt.cdc.gov/radiation/arsphysicianfactsheet.asp, Page last reviewed: Oct. 22, 2013, Page last updated: Aug. 21, 2014.
CDC, 2014, "Questions and Answers on Ebola", CDC: Page last reviewed: Oct. 24, 2014, Page last updated: Oct. 24, 2014.
CDC, 2014, "Signs and Symptoms of Ebola", CDC: Page last reviewed: Oct. 18, 2014, Page last updated: Oct. 18, 2014.
Chen, 2014, "Edaravone Protects Human Peripheral Blood Lymphocytes from Gamma Irradiation-induced Apoptosis and DNA Damage", Cell Stress Chaperones, Sep. 3, 2014.
Gaugler, 2005, "A Unifying System: Does the Vascular Endothelium Have a Role to Play in Multi-organ Failure Following Radiation Exposure?", BJR Suppl. 2005;27:100-5.
Higgins, 2014, "Ebola Facts: How Many Ebola Cases are Outside of West Africa?", By Andrew Higgins Oct. 17, 2014, New York Times.
Hutchinson, 2007, "Cytokine and Chemokine Expression in Humans Infected with Sudan Ebola Virus", Reprints or correspondence: Dr. Karen L. Hutchinson, Special Pathogens Branch, MS G-14, Centers for Disease Control and Prevention, 1600 Clifton Rd. NE, Atlanta, GA 30333 (kbh6@cdc.gov).
Kalamida, 2014, "Important Role of Autophagy in Endothelial Cell Response to Ionizing Radiation", PLoS ONE 9(7): e102408. doi:10.1371/journal.pone.0102408.
Kelland, 2014, "More Cases of Ebola in Europe 'Unavoidable', WHO says", Reuters.com, Kate's Feed EMEA Health and Science Correspondent, Oct. 8, 2014.
King, 2014, "Ebola Virus Infection", http://emedicine.medscape.com/article/216288-overview.
Li, 2006, "The Preclinical and Clinical Trial of Platelet Substitute-Fibrinoplate", 4th Asian Pacific Congress on Thrombosis and Haemostasis, Suzhou, China, Sep. 23, 2006.
Rithidech, 2012, "Attenuation of Oxidative Damage and Inflammatory Responses by Apigenin Given to Mice After Irradiation", Mutat Res. Dec. 12, 2012;749(1-2):29-38. doi: 10.1016/j.mrgentox.2012.08.001. Epub Aug. 15, 2012.
Sanchez, 2004, "Analysis of Human Peripheral Blood Samples from Fatal and Nonfatal Cases of Ebola (Sudan) Hemorrhagic Fever: Cellular Responses, Virus Load, and Nitric Oxide Levels", J. Virol. Oct. 2004 vol. 78 No. 19 10370-10377.
Sullican, 2003, "Ebola Virus Pathogenesis: Implications for Vaccines and Therapies", doi: 10.1128/JVI.77.18.9733-9737.2003, J. Virol. Sep. 2003 vol. 77 No. 18 9733-9737.
Sung, 2014, "Fibrinogen Coasted Nanospheres Prevent Thrombocytopenia-related Bleeding", American Society of Hematologists annual meeting, Dec. 2014.
Winslow, 2013, "Oxygen: the Poison is in the Dose, Transfusion", Feb. 2013;53(2):424-37, doi: 10.1111/1.1537-2995.2012.03774.x. Epub Jul. 15, 2012.
Yang, 1998, "Distinct Cellular Interactions of Secreted and Transmembrane Ebola Virus Glycoproteins", Science Feb. 13, 1998:279 (5353):1034-7.
Yen, 1995, "A Novel Approach to Correcting the Bleeding Associated with Thrombocytopenia", Presented to American Association of Blood Banks: 48th annual meeting, Nov. 11-15, 1995.
Kutler et al., Annu Rev Med; 2009, 60:193-206.
Yasukochi et al., "Radiation-induced skin ulcer and rib fractures following percutaneous coronary internetion (PCI): A case of right back skin ulcer and adjacent rib fracture after single PCI", J. Dermatol, Mar. 20, 2015, doi: 10.1111/1346-8138.12839.
Shope et al., "Radiation-induced Skin Injuries from Fluoroscopy", RadioGraphy 1996, 16:1195-1199.
Xiao We Mao et al., "Effects of Fibrinoplate-S in a Radiated Mice Model", an abstract at the Radiation Research Society Annual Meeting held in Weston, FL, Sep. 19-22, 2015.
Nauth et al., "Stem Cells for the Repair and Regeneration of Bone" published in Indian J Orthop. Jan.-Feb. 2012; 46(1): 19-21.
Teo, A.K.K., et al., 2010 Biochem J 428:11-23 (Year: 2010).
Berg-Foels, W.S.V., 2014 Tissue Engineering Part B, 20(1):28-39 (Year: 2014).
Elzoghby et al., Journal of Controlled Release, 157, 168-182, (Year: 2012).

(56) References Cited

OTHER PUBLICATIONS

Muller et al., Pharmaceutical Research, vol. 13, No. 1, 32-37, (Year: 1996).

* cited by examiner

NANOPARTICLES FOR THE THERAPEUTIC TREATMENT OF RADIATION-INDUCED SKIN ULCERS

CROSS-REFERENCE TO RELATED APPLICATION

This application claims the benefit of priority under 35 U.S.C. § 119(e) based upon U.S. provisional patent application Ser. No. 62/733,468 filed on Sep. 19, 2018. The entire disclosure of the prior provisional application is incorporated herein by reference.

This application claims the benefit of priority of and is a Continuation-In-Part under 35 U.S.C. § 120 based upon co-pending U.S. patent application Ser. No. 15/233,779 filed on Aug. 10, 2016, U.S. patent application Ser. No. 15/618,234 filed on Jun. 9, 2017, U.S. patent application Ser. No. 15/238,928 filed on Aug. 17, 2016, and U.S. patent application Ser. No. 14/956,066 filed on Nov. 27, 2015. The entire disclosures of the prior applications are incorporated herein by reference.

BACKGROUND

Technical Field

The present technology relates to the field of treatment for patients after appearance of a skin ulcer(s) resulting from exposure a high dose of ionizing or cosmic radiation, the treatment resulting in accelerated healing of the skin ulcer.

Background Description

Radiation skin injury is a significant medical and industrial problem. This injury, often called "radiation dermatitis", occurs in about 95% of patients receiving radiation therapy for cancer. Workers in a nuclear plant or citizens living near sites with radioactive material may also accidentally come into physical contact with exposed radioactive material as a result of natural disasters or man-made events. Astronauts on prolong space missions can have exposure to high-velocity cosmic rays: increasing the thickness of shielding material is not practical not only because of the increased weight of the shielding material that needs to be lifted into space, but doubling the mass of shielding material can only reduce the dose of penetrating cosmic radiation by about 10%.

Radiation skin injuries in some ways are different from total body radiation in that the patient's vital organs may be spared (including the bone marrow where new blood cells are to be produced). However, patients suffering from severe cases of radiation skin injuries typically also suffer other injuries, the combined effect can be major morbidity and even mortality. In patients suffering from only radiation skin injury, the result ranges in severity: from mild erythema to moist desquamation and ulceration. Currently, there are no effective treatments to prevent the ill effects after radiation skin injury has occurred.

While the term "radiation skin injury" may mean any and all kinds of injury to the skin caused by radiation, one severe kind of radiation skin injury is "radiation-induced skin ulcer" (RSU) where the affected skin actually becomes ulcerated. RSU is very painful and is often misdiagnosed causing delay in proper treatment. At the present time, the only "treatment" is plastic surgery where the surgeon will try to create a "flap" by moving a healthier piece of tissue nearby to cover the ulcer. The "flap" needs to have its blood vessels and nerves still connected (to its original supplies) so that the relocated flap can survive. However, given the weakened state of many of these patients, the transposed flap often fails. The plastic surgery itself can be very expensive and poses an additional safety risk because general anesthesia is required.

One attempt to mitigate the severity of radiation skin injury was reported by Takikawa M et al. in J Radiat Res. 2012; 53(3):385-94. "Protective Effect of Prostaglandin E1 on Radiation-Induced Proliferative Inhibition and Apoptosis in Keratinocytes and Healing of Radiation-Induced Skin Injury in Rats." They reported that X-irradiation at a dose of 20 Gy induced epilation, minor erosions, and skin ulcers in rats. Prostaglandin E1 has some protective effect only if it is administered 30 minutes to one hour before irradiation. It apparently has no beneficial effect when administered after exposure of the skin to a high dose of radiation. Since few patients know when they will come into contact with a highly radioactive material, this compound is of limited use in realistic situations.

In U.S. Pat. No. 9,629,931 "Nanoparticles for the treatment of radiation skin injury" Yen disclosed a method of using fibrinogen-coated albumin spheres (FAS) to treat patients immediately before the application of radiation or immediately after radiation exposure. That disclosure did not teach how to treat patient after the skin ulcer has appeared and showed no data on whether treatment with FAS can be effective after the skin ulcer has appeared. Given the fact that the ulcer typically appears many weeks after exposure to radiation (and is often misdiagnosed, causing further delay) it is not obvious at all if FAS can still be effective in healing the ulcer when administered so long after the radiation injury. Therefore, there is need for an effective treatment, which can be administered to patients who have developed a visible skin ulcer due to radiation exposure, without the need of knowing when the radiation exposure occurs.

While the above-described devices fulfill their respective, particular objectives and requirements, the aforementioned patents do not describe nanoparticles for the therapeutic treatment of radiation-induced skin ulcers.

Therefore, a need exists for new and novel nanoparticles for the therapeutic treatment of radiation-induced skin ulcers. In this regard, the present technology substantially fulfills this need. In this respect, the nanoparticles for the therapeutic treatment of radiation-induced skin ulcers according to the present technology substantially departs from the conventional concepts and designs of the prior art, and in doing so provides an apparatus primarily developed for the purpose of therapeutic treatment of radiation-induced skin ulcers.

BRIEF SUMMARY OF THE PRESENT TECHNOLOGY

In view of the foregoing disadvantages inherent in the known types of radiation skin injury mitigation systems or methods now present in the prior art, the present technology provides a novel nanoparticles for the therapeutic treatment of radiation-induced skin ulcers, and overcomes the above-mentioned disadvantages and drawbacks of the prior art. As such, the general purpose of the present technology, which will be described subsequently in greater detail, is to provide a new and novel nanoparticles for the therapeutic treatment of radiation-induced skin ulcers and method which has all the advantages of the prior art mentioned heretofore and many novel features that result in a nanoparticles for the therapeutic treatment of radiation-induced skin ulcers which is not anticipated, rendered obvious, suggested, or even implied by the prior art, either alone or in any combination thereof.

Submicron albumin particles called nanoparticles, which are coated or not coated with coagulation factors, are effective in reducing the morbidity and mortality associated with radiation-induced skin ulcer(s) (RSU) after the ulcer(s) become visible to the naked eye. Success of the present technology does not require knowledge on the dose of irradiation, or the time of exposure to the radiation, or the fact that the patient has indeed been exposed to radiation. The dose is to be administered intravenously within one day of the appearance of the skin ulcer and is effective at a dose of 8 to 16 mg per kg weight of the patient, given one or multiple times directly into a vein with or without the presence of a pre-existing intravenous fluid line According to one aspect of the present technology, the present technology can include a method of treating radiation-induced skin toxicity or skin ulcer with nanoparticles. The method can include the steps of providing a suspension including fibrinogen-coated albumin nanospheres and one of sorbitol or caprylate. Then treating a patient after exposure to ionizing radiation by administering intravenously the suspension to the patient at a concentration of the fibrinogen-coated albumin nanospheres sufficient to at least one of promote healing of the skin toxicity or reduce a size of the ulcer.

According to another aspect of the present technology, the present technology can include a method of treating radiation-induced skin toxicity or skin ulcer with nanoparticles. The method can include the steps of providing a suspension including fibrinogen-coated albumin nanospheres and one of sorbitol or caprylate. Then treating a patient after exposure to ionizing radiation and after an onset of radiation-induced skin toxicity or a radiation-induced skin ulcer by administering intravenously the suspension to the patient at a concentration of the fibrinogen-coated albumin nanospheres sufficient to at least one of promote healing of the skin toxicity or reduce a size of the ulcer.

According to yet another aspect of the present technology, the present technology can include a method of treating a patient to reduce an amount of blood loss in an organ of the patient. The method can include the steps of providing a suspension including fibrinogen-coated albumin nanospheres and one of sorbitol or caprylate. Then treating a patient by administering intravenously the suspension to the patient at a concentration of the fibrinogen-coated albumin nanospheres sufficient to interact in vivo with an endothelium of blood vessels to reduce blood loss in an organ of the patient.

According to yet another aspect of the present technology, the present technology can include a method of treating a patient to mobilize stem cells or progenitor cells to accelerate healing of a wound. The method can include the steps of providing a suspension including fibrinogen-coated albumin nanospheres and one of sorbitol or caprylate. Then treating a patient by administering intravenously the suspension to the patient at a concentration of the fibrinogen-coated albumin nanospheres sufficient to mobilize stem cells or progenitor cells of the patient to accelerate healing of a wound of the patient.

In some embodiment of the present technology, the fibrinogen-coated albumin nanospheres can be prepared from soluble proteins without an addition of surfactants or detergents.

In some embodiment of the present technology, the fibrinogen-coated albumin nanospheres can be prepared using a human serum albumin solution.

In some embodiment of the present technology, the fibrinogen-coated albumin nanospheres can be prepared utilizing fibrinogen at a ratio of 2.5 parts fibrinogen per 100 parts of albumin spheres (w/w).

In some embodiment of the present technology, the fibrinogen-coated albumin nanospheres can be prepared utilizing fibrinogen at a ratio of 5 parts fibrinogen per 100 parts of albumin spheres (w/w).

In some embodiment of the present technology, the concentration of the fibrinogen-coated albumin nanospheres in the suspension can be 8 to 16 mg per kg of weight of the patient.

In some embodiment of the present technology, the suspension can be prepared by adding a glutaraldehyde solution to an albumin solution and mixed to produce a first solution, and then adding an alcohol solution of ethyl alcohol, sodium chloride and glutaraldehyde to the first solution to produce an initial suspension.

In some embodiment of the present technology, the sorbitol or caprylate can be added to the initial suspension to produce the suspension.

In some embodiment of the present technology, the suspension can be administered intravenously to the patient within one to two days of an appearance of the skin toxicity or the skin ulcer.

In some embodiment of the present technology, the skin toxicity can be selected from the group consisting of transient erythema, dry desquarmation, moist desquarmation, thinning of dermal tissue, dermal atrophy, and dermal necrosis.

In some embodiment of the present technology, the concentration of the fibrinogen-coated albumin nanospheres in the suspension can be 2 ml/kg to reduce blood loss in the organ.

In some embodiment of the present technology, the organ of can be the liver including a laceration.

In some embodiment of the present technology, the fibrinogen-coated albumin nanospheres can be configured to attach to progenitor cells in vivo. The fibrinogen-coated albumin nanospheres can be configured to attach to the progenitor cells through IIb/IIIa cell receptors of the progenitor cells.

In some embodiment of the present technology, the fibrinogen-coated albumin nanospheres can be configured to stimulate or mobilize of endothelial progenitor cells on the endothelium. The endothelial progenitor cells can include pre-existing precursor cells located on the endothelium that are stimulated or mobilized by the fibrinogen-coated albumin nanospheres for deployment to a wound of the patient.

In some embodiment of the present technology, the fibrinogen-coated albumin nanospheres can be configured to reduce blood loss in an organ of the patient by forming co-aggregates in vivo with activated platelets on the endothelium.

There has thus been outlined, rather broadly, features of the present technology in order that the detailed description thereof that follows may be better understood and in order that the present contribution to the art may be better appreciated. There are, of course, additional features of the present technology that will be described hereinafter and which will form the subject matter of the claims attached.

Numerous objects, features and advantages of the present technology will be readily apparent to those of ordinary skill in the art upon a reading of the following detailed description of the present technology, but nonetheless illustrative, embodiments of the present technology when taken in conjunction with the accompanying drawings.

As such, those skilled in the art will appreciate that the conception, upon which this disclosure is based, may readily be utilized as a basis for the designing of other structures, methods and systems for carrying out the several purposes of the present technology. It is, therefore, that the claims be regarded as including such equivalent constructions insofar as they do not depart from the spirit and scope of the present technology.

It is therefore an object of the present technology to provide a new and novel nanoparticles for the therapeutic treatment of radiation-induced skin ulcers that has all of the advantages of the prior art radiation skin injury mitigation systems or methods and none of the disadvantages.

It is another object of the present technology to provide new and novel nanoparticles for the therapeutic treatment of radiation-induced skin ulcers that may be easily and efficiently manufactured and marketed.

An even further object of the present technology is to provide a new and novel nanoparticles for the therapeutic treatment of radiation-induced skin ulcers that has a low cost of manufacture with regard to both materials and labor, and which accordingly is then susceptible of low prices of sale to the consuming public, thereby making such nanoparticles for the therapeutic treatment of radiation-induced skin ulcers economically available to the buying public.

Still another object of the present technology is to provide a new nanoparticles for the therapeutic treatment of radiation-induced skin ulcers that provides in the apparatuses and methods of the prior art some of the advantages thereof, while simultaneously overcoming some of the disadvantages normally associated therewith.

These together with other objects of the present technology, along with the various features of novelty that characterize the present technology, are pointed out with particularity in the claims annexed to and forming a part of this disclosure. For a better understanding of the present technology, its operating advantages and the specific objects attained by its uses, reference should be made to the accompanying drawings and descriptive matter in which there are illustrated embodiments of the present technology.

BRIEF DESCRIPTION OF THE DRAWINGS

The present technology will be better understood and objects other than those set forth above will become apparent when consideration is given to the following detailed description thereof. Such description makes reference to the annexed drawings wherein.

The same reference numerals refer to the same parts throughout the various figures.

DETAILED DESCRIPTION OF THE PRESENT TECHNOLOGY

Figure 1:
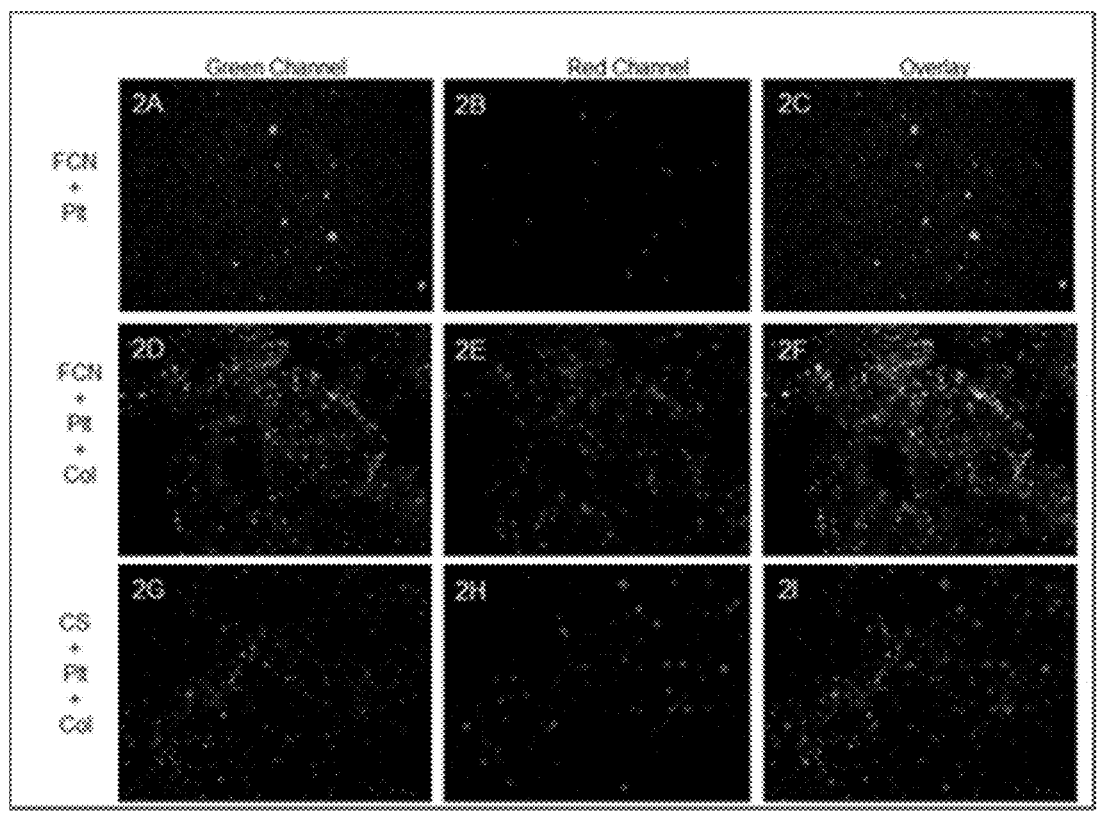
FIG. 1 is a reproduction of prior art from FIG. 2 of Sung et al., "Fibrinogen Coated Nanospheres Prevent Thrombocytopenic-related Bleeding" ASH meeting December 2014.

Referring now to the drawings, and particularly to FIGS. 1-4, an embodiment of the nanoparticles for the therapeutic treatment of radiation-induced skin ulcers of the present technology is shown and generally described herewith.

Although specific embodiments of the present technology will now be described, it should be understood that such embodiments are by way of example only and merely illustrative of but a small number of the many possible specific embodiments which can represent applications of the principles of the present technology. Various changes and modifications obvious to one skilled in the art to which the present technology pertains are deemed to be within the spirit, scope and contemplation of the present technology as further defined in the claims or appended claims.

The present technology deals with treatment of patients exposed to doses of ionizing or cosmic radiation in high enough doses to cause radiation-induced skin ulcer(s) (RSU), with or without concomitant physical or medical injuries to internal organs or other parts of the body. The present technology is a method of producing submicron nanoparticles, the nanoparticles themselves (coated with coagulation factors, and not coated with coagulation factors, such as fibrinogen), and the application of nanoparticles intravenously to patients suffering from visible RSU after the ulcer(s) have become visible to the naked eye. The treatment method does not require knowledge about:

(a) the dose of irradiation given to the patient, or how the patient is exposed;

(b) nor when the radiation exposure occurs, i.e. how long ago is the radiation exposure prior to the appearance of the visible skin ulcer; and (c) nor even a determination that the skin ulcer is due to exposure to radiation—a suspicion that the environment of the patient presents a sufficient radiation risk is enough for the patient to be treated. Such "suspicious" environment would include work in a nuclear plant, or travel in space. Although one would hope that machines which detect radiation (e.g. Geiger counters) would be present to warn workers on the presence of unusually high radiation in the neighborhood (either from machines, or natural material, or sun spots) such preventive measure are often not available when needed.

Because the word "administration" or "exposure" can refer to the radiation dose, or to the FAS treatment dose, the inventor wishes to make a distinction of 3 kinds of treatments where FAS can be used for:

1) Prophylactic treatment: this means FAS is administered before the exposure to the high dose of irradiation, whether the doses of irradiation is given intentionally or not. For example, in breast cancer patients, a high proportion of such patients will be given radiation therapy. Despite the efforts of radiation oncologist to use divided radiation doses, about 1% of the irradiated patients will end up with radiation-induced skin ulcers. If the medical community decides that every such patient should be treated with FAS prophylaxis, about 500,000 patients in the USA will be administered FAS, even though many of them (99%) may not ultimately develop radiation-induced skin ulcer.

2) Mitigation: FAS will be administered to patients after their exposure to radiation but only to patients who are suspected of receiving a dose of radiation higher than usual or the patient is weaker than usual. The medical community at this time is not sure of which subpopulation among all the irradiated patients would ultimately develop radiation-induced skin ulcer. Had they known that, they would not have subjected this subpopulation to any radiation at all (or would use a lower divided dose, despite the possibility of inadequate radiation treatment to kill all the cancer cells). For our discussion, if this subpopulation with propensity to develop radiation-induced skin ulcer is 10% of all those who are exposed to irradiation, then every year in the USA, about 50,000 patients will be treated for "Mitigation" of the ill effects of radiation.

3) Therapy: FAS will be administered only to patients after the skin has developed a visible ulcer. Due to the fact that the patient may not be able to report a skin problem immediately upon noticing the ulcer, or the health professional may misdiagnose the skin ulcer as another form of the cancer invading the skin of the patient, this present technology does not demand how soon the treatment must be started, only that the treatment should be started as soon as possible after the ulcer is properly diagnosed.

It should be noted that Yen's disclosure in U.S. Pat. No. 9,629,931 is concerned about the effectiveness of FAS when administered on day 1, 2 before the dose of irradiation and day 1, 2 after the dose of irradiation (please see Experiment 2, group 1 and group 3 in U.S. Pat. No. 9,629,931). There is no teaching on whether FAS is still effective when administered after the ulcer has become visible. While the data in U.S. Pat. No. 9,629,931 show that FAS is effective for prophylaxis and mitigation (as explained in (1) and (2) above), it is not obvious that FAS can still be effective when given weeks later as a therapy (as explained in (3) above.)

The efficacy of FAS for prophylaxis and mitigation of RSU has been presented to a special group at the NASA iTech Forum on Jul. 10-14, 2017, held at the National Institute of Aerospace in Hampton, Va. The Applicant's work has won the honor of being "the Top 10 Most Important Innovation" for the Mars Program by NASA, because there is an urgent need to take care of the problems of prolong radiation exposure by the astronauts, especially on the planned 10 month journey to Mars. The following is the content of the public disclosure. Readers of the present application are advised to pay particular attention to FIG. 4 and the associated explanation why on "Day 14 after irradiation, the control (normal saline) group shows less of an ulcer than the FAS-treated group". Also the term "FCN" (fibrinogen-coated nanospheres) in the White Paper is the same as FAS in this present technology.

WHITE PAPER SUBMISSION FOR NASA iTECH CYCLE 2 (Feb. 23 to Apr. 7, 2017)

1. TITLE: Tissue Regeneration After Radiological and Acute Trauma in Space
2. FULL NAME: Richard C. K. Yen1, Ph.D., M.D.; Xiao Wen Mao2, M.D.
3. AFFILIATED COMPANY: 1Founder and CEO of Fiplate, Inc. (a Nevada corporation), served as senior scientist in JPL, 1981-82; won a NASA award for Innovation in hybrid microsphere.
4. NOT AFFILIATED WITH ANY ACCELERATOR OR INCUBATOR
5. AFFILIATED UNIVERSITY: 1) Previous consultant to a NIAID funded contract (BAA-NIAID-NIHAI-2013166) providing the active substance (fibrinogen-coated albumin nanospheres, FCN) to Duke University, North Carolina for the project: Countermeasures against radiation damage (Contract HHSN272201400034C). 2) Dr. Xiao Wen Mao of Loma Linda University in California did the work on skin ulceration. She agreed to participate/lead in this project.
6. NOT AFFILIATED WITH ANY ANGEL OR VC FIRM.

Introduction:

Trauma experienced by explorers on earth and in space is unlikely to come from one pure source: the victim can have broken bones, burns, crushed internal organs, severe internal bleeding all at the same time. In addition, exposure to radiation will impair wound healing. At the present time, there is no good way to treat trauma in space and no effective mitigation after exposure to high doses of irradiation. A product that is lightweight, easy to administer and can promote healing in wounds caused by multiple etiologies (with and without irradiation) can greatly enhance NASA's program to develop procedures effective in "radiation protection and mitigation."

Fibrinogen-coated albumin nanospheres (FCN) is a novel medical product ready to start Phase I clinical trials in human volunteers. It is a suspension of ready-to-use nanometer-sized albumin spheres capable of interacting in vivo with the endothelium of blood vessels. The interaction has been proven to produce at least two profound effects. (a) It reduces spontaneously the amount of blood loss by 55% in a soft organ such as the liver, without the need for any intervention. At the present time, the standard practice to control bleeding in a lacerated liver is to apply pressure, which would require a surgical operation to expose the liver first. But more importantly, (b) it also mobilizes stem cells or progenitor cells to accelerate the healing of a wound, even after exposure to high doses of irradiation.

Published medical literature has repeatedly shown the importance of (i) stem cells moving from the bone marrow to a wound to transform directly or indirectly into the "end-product" i.e. healthy cell types appropriate for the normal tissues at the previous-wound site. Moreover, (ii) there are pre-existing precursor cells located on the endothelium called Endothelial Progenitor Cells (EPCs) which are responsible for rapid deployment to a wound. Even though they are not technically "stem cells", EPCs have been shown to transform into "end-tissues" e.g. bone structures at the site of a fracture and they are involved in a large number of other healing processes.

History:

FCN is manufactured from clinical-grade human albumin molecules first as nanospheres, and then coated with clinical-grade human fibrinogen. Therefore, it is completely sterile and can be massively produced. It is stable in room temperature for over one year and requires no special conditions of storage. It is originally designed for used in situations where platelets are not available or practical. It will eventually reduce and replace the need for platelet transfusions (which has a market size of over $5 billion worldwide). FCN does not cause alloimmunization as platelet do. It works even in severely thrombocytopenic subjects, which have only 1% of normal platelet counts. Because of their small size, the spheres will circulate rheologically near the endothelium, thus being closer than platelets to endothelial wounds or radiation-induced defects. FCN can carry additional biological molecules and is therefore an excellent delivery system to the endothelium, which is a very important regulator in normal physiology. Remarkably, FCN does not cause random clots. Vigorous tests have shown repeatedly that it is non-thrombogenic. The effective dose is 1 ml (containing 8 mg of nanospheres) per kg weight of the patient. One bottle contains 100 ml of product, enough for administration intravenously to a 100 kg person for immediate effect. In some indications, one dose is effective. In other indications (e.g. improvement in survival) we administered three doses, on day 1, 5, 10 after a lethal dose of irradiation.

Mechanism:

(a) In the reduction of blood loss, FCN works by forming co-aggregates in vivo with activated platelets on the endothelium. In FIG. 1 (reproduced from FIG. 2 of Sung et al., 2014) flow cytometry showed how FCN-platelet coaggregates are formed from a mixture of FCN and platelets on the addition of collagen.

(b) In the mobilization of progenitor cells, the mechanism is through stimulation or mobilization of the EPCs on the endothelium. The Applicant is working to identify the type of cells that FCN can attach to in vivo, probably through the IIb/IIIa cell receptors.

Major Results:

(a) In a model of liver laceration: 20 Sprague Dawley rats (10 each group) were administered (i) 2 ml of FCN/kg in treatment group; or (ii) 2 ml of saline/kg in control group. Under anesthesia, a standard surgical laceration was created in the exposed liver. Blood loss was collected by pre-weighed sponges without interference at the cut.

Figure 2A:
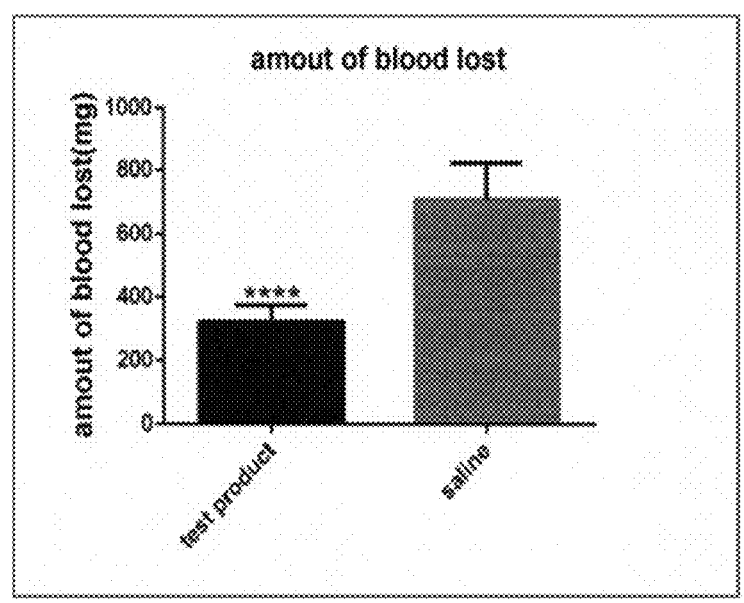
FIG. 2A is a graphical view of the amount of blood loss of a treatment group treated with fibrinogen-coated nanospheres (FCN) of the present technology compared with a control group.
Figure 2B:
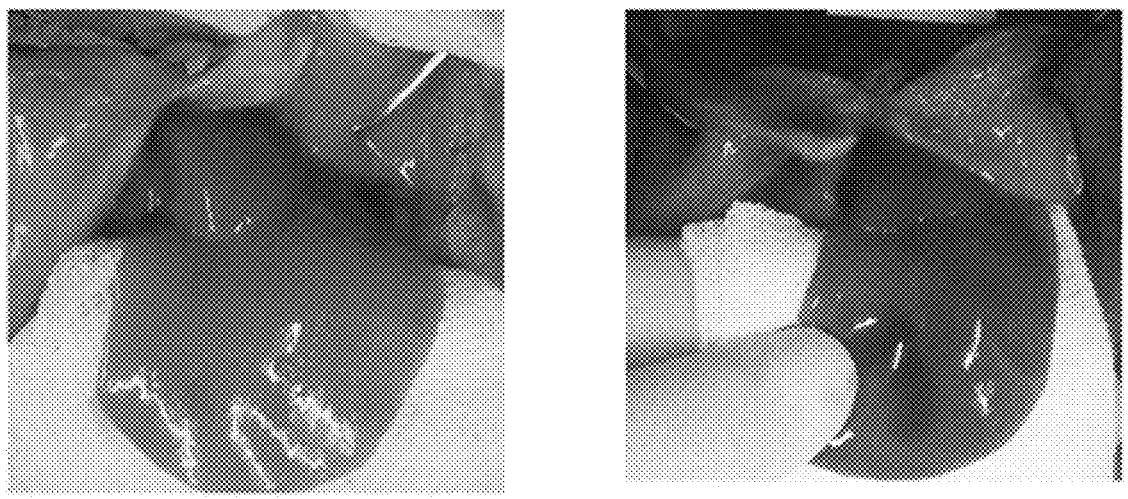
FIG. 2B is a photograph view of an FCN-treated liver (left side of photograph) and the control liver that is still bleeding (right side of photograph).

In FIG. 2A on the left shows a 55% decrease in blood loss in the treatment group (P<0.0001) (Shih and Yen, 2016). In FIG. 2B are photos of the FCN-treated liver (left side of photo) and the control liver (still bleeding, right side of photo).

Figure 3:
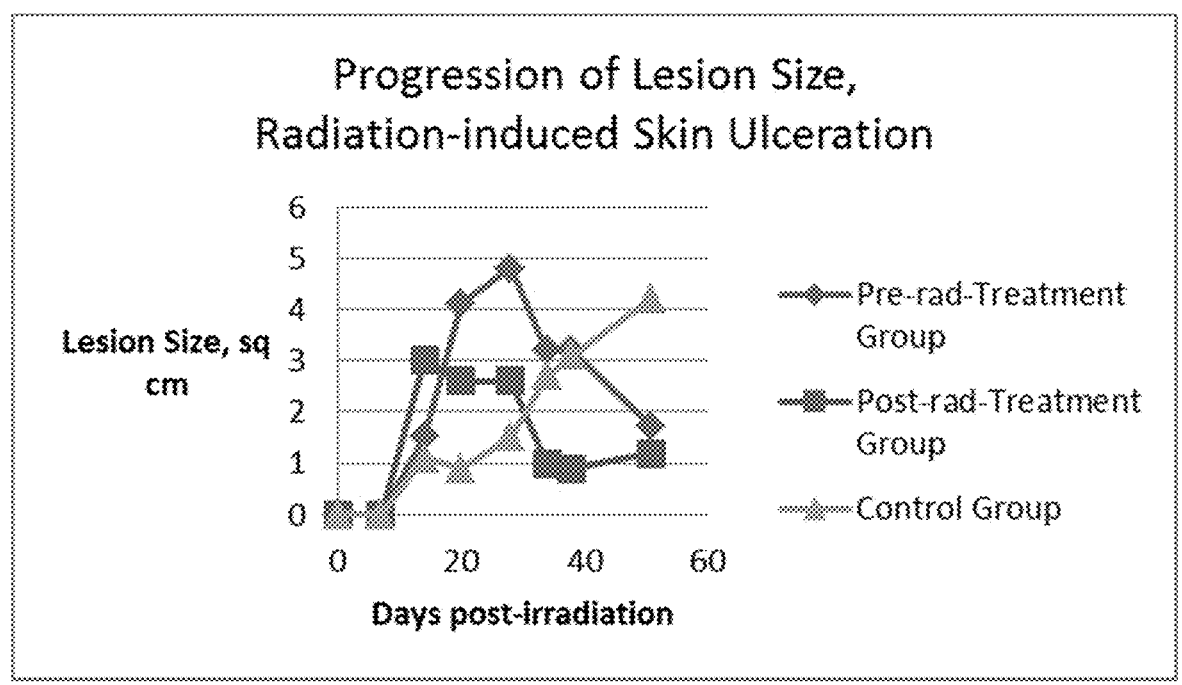
FIG. 3 is a graphical view showing that no skin damage was seen before day 14 of treatment of FCN of the present technology.

(b) In a deep-tissue wound caused by a localized beam of irradiation to the skin, FCN promoted the coordinated healing of multiple tissues in the ulcer, including the skin, fat, muscle, nerve and blood vessels (Mao et al. 2015). A dose of 25 Gy was delivered locally to the hind leg of rats. Treatment was (a) 8 mg FCN intravenously on day −1, −2 pre-irradiation, or (b) day +1,+2 post-irradiation; (c) control groups received saline. No skin damage was seen before day 14, as best shown in FIG. 3. Surprisingly on day 14, ulcers suddenly appeared. Not only that, the post-treatment group (red line) on day 14 had ulcers bigger than the pre-treatment group (blue line), both of which were bigger than the control group (green line). However, by day 51 the ulcers in both treatment groups were healing well while the control group showed no sign of healing. In addition, the ulcer in the post-treatment group appeared to be shrinking after day 14 while the pre-treatment group was only beginning to develop after day 14. The ulcer in the pre-treatment group became maximal on day 28. This is important because in a non-irradiated animal, this is the amount of time for the basal cells of the epidermis to reach the surface of the skin. After day 28 the ulcer size in the pre-treatment group decreased. The data confirmed what was expected of stem cells working beneath surface of the skin.

Figure 4:
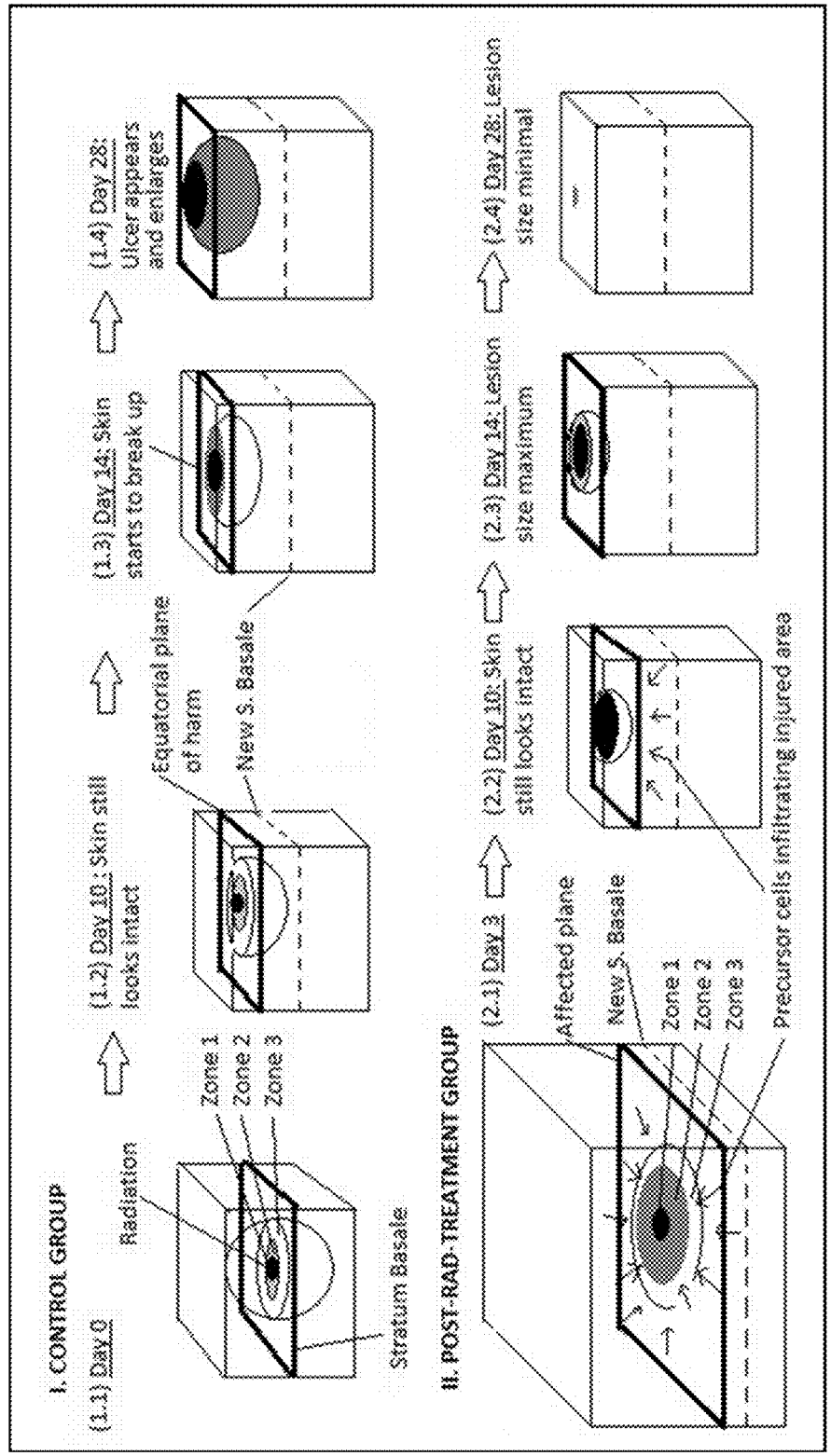
FIG. 4 is a schematic view explaining the observations on day 14 and thereafter of treatment of FCN of the present technology.

FIG. 4 explains the observations on day 14 and thereafter. In the normal epidermis, there are 5 layers of cells, the bottom layer being the basal (stem) cells (stratum basale) whose division will push the other layers upward toward the surface. In the non-irradiated subject, this process takes about 28 days. In the control group where there is irradiation without mitigation, the basal cells are affected the most on day zero. In subsequent days the damage will spread, mainly horizontally from zone 1 to 3. The layers above the basal cells are dying cells and so they are little affected by radiation. Since the dermis layer below the basal cells is also harmed by the pulse of radiation, any new basal cells formed in subsequent days will not get enough nutrients; therefore further slowing the "upward push" of all the cells (dead or alive).

As a result, some of the dead cells in this group only began to show up at the surface on day 28 but the ulcer size will continue to expand beyond day 51. In contrast, in the post-treatment group, a few days after irradiation (e.g. day 3) the stem cells have begun infiltrating the damaged areas. This will (a) limit the size of the ulcer (the horizontal dimension) and (b) accelerate the upper push (due to increased mitotic activity of these infiltrating stem cells). Therefore, the ulcer appears sooner but its maximal size is smaller than the other groups. Because of the healing effect of the infiltrating stem cells, the size of the ulcer in this post-treatment group gets smaller by the day after day 14. This situation is confirmed by the development of the ulcer in the pre-treatment group (not shown in FIG. 4). Since the pre-treatment group had their stem cells mobilized before the burst of irradiation was given, and stem cells are very sensitive to the effects of irradiation, this group had a reduced number of stem cells available to mitigate the harm inflicted on day zero. A detail analysis of another system (the development of various subsets of white cells, the data are not shown here) also indicates that stem cells of that lineage are affected on day zero by irradiation. Similarly, the effect of FCN on stem cells in that system can also be detected up to day 51. The combination of data from 2 systems suggest strongly that FCN can mobilize stem/progenitor cells, resulting in faster healing. This means FCN would be beneficial in regenerative medicine, such as for treating patients with severe spinal cord injury, crushed bones, and Alzheimer's disease.

Other Relevant Information:

Toxicology of FCN has been studied using 5 doses over 15 days at 8, 16, 24 mg/kg in mice. There is no clinical sign or any pathology noted.

Summary/Matrix:

(a) The present technology focuses on "radiation protection and mitigation": in particular, it provides data on wound healing after radiation exposure. The results of FCN application particularly after a high dose of irradiation clearly show mitigation of damage. The treatment with FCN results in healing 3.6 times faster (peak at day 14) than the control (no healing even on day 51).

(b) The product will break new grounds. There is no approved product yet which can have multiple benefits (and indications) including (i) control bleeding immediately and spontaneously in a soft-organ trauma model; and (ii) also enhances healing after radiation exposure.

(c) The FCN of the present technology is ready to start clinical trial phase one. The present technology product has already been designated Orphan Medicinal Product for "treatment of acute radiation syndrome" by the EMA on Aug. 10, 2015 (EU/3/15/1535). The company already accepted a bid from Parexel International to start the trial in Pasadena, Calif. as soon as funding is available.

(d) FCN of the present technology will fill the unmet market needs for platelets. The market size for platelet transfusion is about US $5 billion worldwide. The product of the present technology can be shipped via postal service, such as but not limited to, FedEx directly to hospitals and other points of use. It is a one-compound-multiple-indication product expected to be useful also for burn and ICU patients.

(e) The customers can be hospitals, physicians, treatment facilities and the like who will benefit from discharging patients earlier and to prevent alloimmunization of patient due to the present practice of platelet transfusion.

(f) Person(s) and/or organization(s), such as but not limited to, Loma Linda and Duke University are well staffed and equipped for radiation-related research. The present technology has been under development since 1982 and has more than 20 patents to protect this technology. A manufacturing facility has been built in Las Vegas, Nev.

(g) The present technology has a clear vision: the path is (i) line up a contract research organization (CRO) to do clinical trials (e.g. on treatment of acute radiation syndrome" (ii) get European Medicines Agency (EMA) to approve clinical plan, (iii) proceed with the orphan drug pathway to approval, (iv) publicize through medical conventions and journals, (v) ship the product of the present technology to customers.

(h) The leadership has been proven: National Institutes of Health (NIH) already spent US $4 million on this project with a contract for the Duke team to confirm initial findings. The present inventor and staff have won numerous awards and have been invited by 4 regional governments in China to start a company there.

The present technology has been found to be effective in the therapeutic treatment of a number of signs and symptoms related to RSU.

It should be noted that the following statement appears in the Yen disclosure of U.S. Pat. No. 9,629,931: "The present technology is effective when given as a prophylactic measure, i.e. administered before the time of exposure to radiation. Significantly, the present technology is also effective when administered at various times after the patient's exposure to high doses of radiation" (third paragraph in "Detailed Description of the Invention"). However, there is no suggestion in U.S. Pat. No. 9,629,931 that the author intends to use FAS to treat the ulcer after the ulcer becomes visible. The reference to "at various times after the patient's exposure to high doses of radiation" is a reference to the time of administration of FAS with respect to the time of exposure to high doses of radiation, i.e. according to that disclosure, the "post-radiation" administration of FAS is not restricted to day +1 and day +2, but can be later than day +2 after radiation. Since the appearance of the ulcer in the human population can be months after the dose of radiation, it is not obvious from the prior art that FAS can be effective when administered at a time after the ulcer appears.

Therapeutic treatment with the present technology reduces the signs and symptoms of RSU. Often a patient may not even be aware of his exposure at the time of exposure—that he has touched or has been exposed to a highly radioactive substance, because the exposure causes no pain or other sensations.

The time course of radiation dermatitis is well known. Inflammatory erythema develops on the skin within about a week after a high dose of irradiation. The subsequent healing may still result in desquamation and pigmentation. With progressively higher doses of irradiation, blisters may develop, followed by atrophy, teleangiectasia, and irregular hyperpigmentation. The present technology does not preclude the administration of FAS to treat these signs and symptoms. However, with RSU, typically caused by still higher doses of exposure, ulceration occurs. With the formation of ulcers, the blood supply is compromised: therefore, it is difficult for the body to bring nutrients and healing to the site. Since there is little or no blood flow to the center of the ulcer, the ulcer will not receive platelets: therefore, the mechanism of action by the formation of co-aggregates with activated platelets does not appear to be involved here. (For a discussion of the mechanism of action, of which there are at least two modes, please see discussion in White Paper to NASA iTech).

The healing of the ulcer (decrease in size, and reduced pain) probably is mediated by the mobilization of stem cells or endothelial progenitor cells (EPC). This is because the affected tissues (skin, fat, muscles, nerves, blood vessels) all heal and they heal in a coordinated manner. Stem cells or their progenies (partially committed, slightly more mature cells) typically originate from other sites, but when they arrive at a wound or ulcer, they receive the signals from the location as to what they should become—depending on the local tissue or cellular environment, a stem cell may become a nerve cell or a muscle cell. The data presented in White Paper showed that these stem cells are obviously mobilized by the administration of FAS around the time of radiation exposure. This is so because the healing of the ulcer is faster when FAS is administered post-radiation, rather than pre-irradiation. The slower healing in the case of prophylaxis (FAS given before the radiation exposure) is because the radiation will kill at least some of the mobilized stem cells. (Stem cells and all immature cells are designed for fast reproduction and they are most prone to damage by radiation). Having fewer viable stem cells that can regenerate into healthy tissues accounts for the slower healing when FAS is administered before the exposure to radiation.

The data presented in the White Paper: Figure "Progression of Lesion Size" show also that in the control (saline-treated) group, the ulcer continues to expand on Day 51 with no sign of healing. With each patient, the tolerance with a skin lesion may be different. Some may see a doctor immediately while others may talk themselves out of seeing a doctor. The present technology does not place a limit on how soon FAS must be administered after RSU is diagnosed. The FAS should be administered as soon as RSU is suspected.

The science of measuring or detecting how much radiation a person has received is still immature. Even if progress can be made soon, it is hard to estimate how much of the radiation has affected the vital organs including the bone marrow, as compared to the radiation having hit less vital parts of the body. A person exposed to radiation on the skin should be regarded as a person who has been exposed to more areas than the skin. Therefore, by the time a patient shows signs and symptoms of radiation skin injury, he should be treated for more than the skin injury. In other words, RSU may serve as an early warning sign that the patient may have been exposed to total-body irradiation: the patient may be in deeper trouble than is shown on the skin. Healthy providers should consider treatment for more severe problems than for the skin alone.

Experiment One:
Manufacture of Submicron-Size Nanoparticles Small Enough to Remain in Suspension for Over a Year at Room Temperature
Purpose:

To disclose the method of mass production of a suspension of particles that are essentially spherical and with an average diameter of less than one micron, manufactured from a high concentration of animal albumin.

Material and Method:

Bovine serum albumin powder was purchased from Boval Company LP, Cleburne, Texas and dissolved in water to result in an 18% solution. The solution will be further processed as follows without the addition of surfactants or detergents. Glutaraldehyde solution was purchased from Sigma-Aldrich, St. Louis, Mo. 63103 and diluted to 0.15 mg per ml with water. An alcohol solution/mixture (containing ethyl alcohol, sodium chloride, glutaraldehyde, all three substance at various concentrations, with the balance being water, hereafter called "EG") was prepared as follows: 2850 ml of 100% ethanol USP grade was mixed with 950 ml of water, after which 7.6 ml of a glutaraldehyde solution (25%) and 114 ml of a sodium chloride solution (0.9%, USP) was added to result in 3921.6 ml of EG solution. Sorbitol powder USP grade was purchased from Sigma-Aldrich and dissolved in water to form a 25% solution. Sodium caprylate was purchased from Jost Chemical Co., St. Louis, Mo. 63114 and dissolved in water to form a 10% solution.

The following steps were done at room temperature, 19° to 24° Centigrade under sterile conditions. All the solutions were filtered via 0.2 micron filters before mixing in a class-100 clean room. At time zero (0), 190 ml of glutaraldehyde solution (0.15 mg/ml) was added to 381 ml of bovine serum albumin solution (18%) and well mixed in the container. Within 3 minutes, 3426 ml of EG was added and well mixed, at which time the solution turned turbid indicating the formation of spheres.

After one hour, the suspension was dialyzed in distilled water to remove the EG. After measuring the concentration of the spheres in the dialyzed suspension, sorbitol, caprylate and an additional aliquot of distilled water were added to the dialyzed suspension to result in a final concentration, respectively, of 5% sorbitol, 13.3 mg of caprylate per gram of total protein, and 8 mg of spheres/ml of suspension.

The suspension was subsequently filled into sterile containers, capped and sealed. Then the product was terminally sterilized by heating the suspension inside the container to 60° Centigrade for 10 hours, or pressurized up to 600 MPa.

Results:

Analysis of the suspension showed that the particles are spherical and the median diameter was about 0.35 micron, with less than 1% of the spheres with a diameter greater than one micron. No aggregates were observed. The suspension was stable after one year of storage in room temperature without constant agitation to keep the particles in suspension. There was no significant shift of size distribution of particles after one year of storage at room temperature.

The suspension was frozen and kept frozen at minus 18° Centigrade for at least one year. Then samples were thawed and stored at room temperature for at least one year. Analysis of the size distribution of particles showed no significant change from the size distribution of particles in suspensions analyzed within days of completion of synthesis and terminal sterilization.

Comments:

1. Although bovine albumin solutions are used in this experiment, it is anticipated a number of other albumin solutions can be used, including human serum albumin (dialyzed in distilled water, or not dialyzed), other natural (human or animal) albumin or albumin molecules produced by recombinant-DNA methods. In addition, other proteins may be used to produce spheres with comparable functionality, including fibrinogen, immunoglobulin, collagen, gelatin, as disclosed in U.S. Pat. No. 5,069,936 by Yen.

2. Although the spheres are not further coated with any other biologically active molecules during the manufacturing process in this experiment, it is anticipated that a number of other biologically active molecules, including coagulation factors, such as fibrinogen, vonWillebrand factor, Factor IX and other coagulation factors may be added to the spheres during the manufacturing process. It is expected that various ratios of mixing of the biologically active molecule solution with the sphere suspension is permissible. Specifically, experiments have been conducted where, for example, a solution of fibrinogen up to 3 mg/ml may be mixed at a ratio of 1 part (by volume) of the fibrinogen solution to 4 parts (by volume) of the sphere suspension (the turbid suspension after addition of EG, and before dialysis of the EG-containing suspension with distilled water) to result in "coated spheres." See International Patent Application Number PCT/US2008/006014 by Yen.

3. Although a specific concentration of ingredient solutions are mentioned here as an example, other higher or lower concentrations can be used when combined with a compatible compensating concentration of other ingredients. For example, albumin solutions can vary between 5% to 20% in initial concentration before the addition of a glutaraldehyde solution, which can vary from 0.05 to 0.5 mg/ml. The concentration of ethanol in the EG mix can vary from 55% to 100%, while the glutaraldehyde concentration in EG can vary from 0.1 mg to 0.75 mg/ml and the sodium chloride concentration can vary from 0.5 to 0.005 mg/ml in the EG mix.

4. It is surprising that a suspension of protein spheres can undergo heating at 60° Centigrade for 10 hours without forming aggregates or clumps. The addition of sorbitol together with caprylate probably has a synergistic effect on protecting the protein spheres from aggregation or expression of new antigenic sites during the process of heating and subsequent cooling to room temperature.

Experiment Two:

Improvement in Healing Rates and the Degree of Healing by the Therapeutic Treatment with Submicron Particles After the Ulcer has Become Visible Purpose:

To find out: (a) if a regiment of therapeutic treatment using one single injection (8 and 16 mg of FAS per kg) can improve the rate of healing after the ulcer has appeared; and (b) whether the results are the same when FAS is administered at a late phase e.g. 2 months after the appearance of the ulcer as compared to being administered within 1 week of the appearance of the ulcer Material and Method:

Submicron nanoparticles were synthesized as in Experiment One similar to the procedures published in U.S. Pat. No. 9,629,931, except that human serum albumin (5.5% solution) is used instead of bovine serum albumin (18%.) and the spheres have been coated with fibrinogen at a ratio of 5 parts fibrinogen per 100 parts of albumin spheres (w/w).

Sprague Dawley rats were used, 10 rats per group. Test articles (8 or 16 mg of submicron particles per kg) and control solution (a 5% sorbitol solution, given at the equivalent volume as the test article per kg weight of the animal) were administered intravenously to animals within one to two days of the appearance of the RSU (which typically become visible to the naked eye after day 14 after irradiation).

Since not all ulcers appear on the same day after irradiation, the term "day" in the following discussion applies as follows: Day zero (0) is the day when the ulcer or skin damage is apparent to the unaided eye, regardless of how many days after the irradiation event it happened.

The groups are as follows:

Group One: One dose of submicron particles administered on Day 1, at 8 mg per kg of the weight of the animal.

Group Two: Two doses of submicron particles, administered on Day 1 and 2, at 8 mg per kg each dose.

Group Three: Two doses of control solution administered on Day 1 and 2, at 1 mL volume per kg each dose.

Group Four: Two doses of submicron particles (8 mg per mL) administered on Day 14 and 15 (after appearance of ulcer) each at 1 mL per kg wt. of the animal.

Group Five: Two doses of control solution administered on Day 14 and 15, each at 1 mL volume per kg of the animal.

Group Six: No irradiation, treatment with control solution on day 1 and 2, 1 mL per kg.

The radiation dose was 30 Gy gamma rays, delivered to one hind leg. The study endpoint was acute skin toxicity. The rats were euthanized at 60 days post irradiation. Onset of skin toxicity (transient erythema, dry or moist desquarmation, thinning of the dermal tissue, dermal atrophy and necrosis), their severity and the rate of healing were recorded, with observations made daily.

Results:

The results showed that the rats in all groups, except Group Six, which received no irradiation, all 1, showed severe RSU on the irradiated leg within one month of the exposure to irradiation. There was no RSU on the other, non-irradiated leg.

Comparison of the Results:

The size of the ulcers in Group 1 and 2 begin to decrease immediately after the administration of the submicron particles, so that when measured on Day 6, the ulcer sizes on the average are about 50% that of the sizes on Day zero (0). The improvement in healing in Group 2 may be faster than in Group 1, however, the difference may not be statistically significant due to the small number of animals used in these experiments. However, the ulcers in Group 3 continue to expand after Day zero (0) and when measured on day 6 are on the average about 150% that of the sizes of the same ulcer on Day zero (0)in these animals. The rate of healing and the size of the ulcers between Group 1 and 3 (and Group 2 and 3) are highly statistically significant ($P<0.05$)

By the time Group 4 animals receive submicron particle treatment, their ulcer sizes are about 250% that of the sizes in Day zero (0). However, after the 2 doses of submicron particles, the ulcer sizes immediately decrease. When measured on day 21, the sizes of the ulcers has decreased to about 125% that of the sizes on Day zero (0). In contrast, the sizes of the ulcer in Group 5 continues to expand to over 350% that of the sizes on day zero (0), when measured on Day 21.

The data show that FAS can have some very positive effects even when administered at a late stage of the ulcer formation (Group Four). When FAS is administered as soon as the ulcer is visible (Group One and Two), the healing rate and the degree of healing of all the involved tissues (skin, blood vessels, muscles, fat) appear to be significantly improved over the control group (Group Three.) There is no evidence that the RSU will heal itself (Group Three and Five.) under these experimental conditions without the administration of FAS.

Comments:

Although we have not presented the data obtained in rats exposed to cosmic rays, the results are similar to those obtained from ionizing radiation. Submicron particles administered intravenously to animals exposed to high doses of ionizing and cosmic radiation on the skin improved their healing rate, and reduced morbidity during the healing process (including possibly less pain or chance of infection). The result of the healing process appears to be superior to that resulting from natural healing without the application of the present technology. More experiments need to be done to see if a higher dose or lower dose of the nanoparticles will provide further improvement.

Although this experiment used submicron particles coated with fibrinogen (FAS), it is possible that submicron particles not pre-coated with fibrinogen or other biologically active molecules during the synthesis steps may be equally effective due to the ability of blank spheres attaching endogenous fibrinogen molecules from the host after intravenous administration into the host.

The long shelf life of this suspension of submicron particles makes this product an outstanding candidate for stockpiling in areas where radioactive chemicals or radioactive materials are stored or used. During and after a disaster, there will not be the usual number of healthy providers who can provide medical care. The sooner a suspected victim is treated, the sooner he will be able to help others rather than staying as a burden. Therefore, even though this present technology is effective long after the time of exposure, we expect the treatment to start as soon as a subject is suspected to have developed RSU.

Experiment Three:

Improvement in Healing Rates and the Degree of Healing by the Therapeutic Treatment with Submicron Particles Containing Less Fibrinogen Per Spheres Purpose:

To find out if a regiment of therapeutic treatment using one single injection (16 mg of FAS per kg) with FAS containing half the "fibrinogen content" can improve the rate of healing after the ulcer has appeared.

Material and Methods:

FAS is manufactured essentially by the same method as in Experiment Two, except that half the concentration of fibrinogen is used to coat the blank spheres, resulting in a "fibrinogen content" of 2.5 parts of fibrinogen per 100 parts of spheres (w/w) or only 2.5 mg of fibrinogen per 100 mg of spheres. The dose used is also 8 to 16 mg spheres/kg weight of the rats and administered on Day 1 and 2 after Day zero (0) which is the day that the ulcer appears on a rat.

Results:

The improvement in ulcer healing and the degree of healing is slightly better in the spheres with 5% by weight of fibrinogen than with spheres with 2.5% by weight of fibrinogen per sphere; however, the difference is statistically insignificant.

Conclusion:

Spheres with 2.5% by weight of fibrinogen (per mg sphere) is effective in a therapeutic treatment of RSU. Spheres with even less fibrinogen contents may be just as effective.

While embodiments of the nanoparticles for the therapeutic treatment of radiation-induced skin ulcers have been described in detail, it should be apparent that modifications and variations thereto are possible, all of which fall within the true spirit and scope of the present technology. With respect to the above description then, it is to be realized that the optimum dimensional relationships for the parts of the present technology, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present technology. For example, any suitable sturdy material may be used instead of the above-described. And although the therapeutic treatment of radiation-induced skin ulcers have been described, it should be appreciated that the nanoparticles of the present technology herein described is also suitable for treating other radiation induced illnesses or complications.

Therefore, the foregoing is considered as illustrative only of the principles of the present technology. Further, since numerous modifications and changes will readily occur to those skilled in the art, it is not desired to limit the present technology to the exact construction and operation shown and described, and accordingly, all suitable modifications and equivalents may be resorted to, falling within the scope of the present technology.

REFERENCES

Mao X et al, "Fibrinoplate-S for the Treatment of Radiation-induced Skin Damage" the 61th Radiation Research Society Annual Meeting, Weston, Fla., Sep. 19-23, 2015.

Shih M S and R C K Yen, "Efficacy of Compound on Hemostasis of Liver Laceration, Study PL15-0273", unpublished communication, 2016.

Sung A et al. "Fibrinogen Coated Nanospheres Prevent Thrombocytopenic-related Bleeding" ASH meeting December 2014.

What is claimed as being new and desired to be protected by Letters Patent of the United States is as follows:

1. A method of treating radiation-induced skin toxicity or skin ulcer with nanoparticles, said method comprising the steps of:
   a) providing a suspension including fibrinogen-coated albumin nanospheres and one of sorbitol or caprylate; and
   b) treating a patient after exposure to ionizing radiation by administering intravenously said suspension to the patient at a concentration of said fibrinogen-coated albumin nanospheres sufficient to at least one of promote healing of radiation-induced skin toxicity or reduce a size of radiation-induced skin ulcer;
   wherein the concentration of said fibrinogen-coated albumin nanospheres in said suspension is 16 mg per kg of weight of the patient.

2. The method according to claim 1, wherein said fibrinogen-coated albumin nanospheres are prepared from soluble proteins without an addition of surfactants or detergents.

3. The method according to claim 1, wherein said fibrinogen-coated albumin nanospheres are prepared using a human serum albumin solution.

4. The method according to claim 1, wherein said fibrinogen-coated albumin nanospheres are prepared by mixing fibrinogen at a ratio of 2.5 parts fibrinogen per 100 parts of albumin nanospheres (w/w).

5. The method according to claim 1, wherein said fibrinogen-coated albumin nanospheres are prepared by mixing fibrinogen at a ratio of 5 parts fibrinogen per 100 parts of albumin nanospheres (w/w).

6. The method according to claim 1, wherein said suspension is prepared by:
   adding a glutaraldehyde solution to an albumin solution and mixing to produce a first solution; and
   adding an alcohol solution of ethyl alcohol, sodium chloride and glutaraldehyde to said first solution to produce an initial suspension.

7. The method according to claim 6, wherein said sorbitol or caprylate is added to said initial suspension to produce said suspension.

8. The method according to claim 1, wherein said suspension is administered intravenously to the patient within one to two days of an appearance of the skin toxicity or the skin ulcer.

9. A method of treating radiation-induced skin toxicity or skin ulcer with nanoparticles, said method comprising the steps of:
   a) providing a suspension including fibrinogen-coated albumin nanospheres, sorbitol and caprylate; and
   b) treating a patient after exposure to ionizing radiation and after an onset of a radiation- induced skin toxicity or a radiation-induced skin ulcer by administering intravenously a dose of 16 mg/kg of said suspension to the patient at a concentration of said fibrinogen-coated albumin nanospheres sufficient to at least one of promote healing of radiation-induced skin toxicity or reduce a size of radiation-induced skin ulcer.

10. The method according to claim 9, wherein said suspension is administered intravenously to the patient within one to two days of an appearance of the skin toxicity or the skin ulcer.

11. The method according to claim 9, wherein said skin toxicity is selected from the group consisting of transient erythema, dry desquarmation, moist desquarmation, thinning of dermal tissue, dermal atrophy, and dermal necrosis.

12. The method according to claim 9, wherein said fibrinogen-coated albumin nanospheres are prepared from soluble proteins without an addition of surfactants or detergents.

13. The method according to claim 9, wherein said fibrinogen-coated albumin nanospheres are prepared using a human serum albumin solution.

14. The method according to claim 9, wherein said fibrinogen-coated albumin nanospheres are prepared by mixing fibrinogen at a ratio of 2.5 parts fibrinogen per 100 parts of albumin nanospheres (w/w).

15. The method according to claim 9, wherein said fibrinogen-coated albumin nanospheres are prepared by mixing fibrinogen at a ratio of 5 parts fibrinogen per 100 parts of albumin nanospheres (w/w).

16. The method according to claim 9, wherein said suspension is prepared by:
   adding a glutaraldehyde solution to an albumin solution and mixing to produce a first solution; and
   adding an alcohol solution of ethyl alcohol, sodium chloride and glutaraldehyde to said first solution to produce an initial suspension.

17. The method according to claim 16, wherein said sorbitol or caprylate is added to said initial suspension to produce said suspension.

* * * * *